United States Patent [19]
Hirt

[11] 4,178,925
[45] Dec. 18, 1979

[54] ADJUSTABLE POST-SURGICAL SHOE
[76] Inventor: Paul R. Hirt, 1 Needle Point La., Willingboro, N.J. 08046
[21] Appl. No.: 884,192
[22] Filed: Mar. 7, 1978
[51] Int. Cl.² .............................................. A61F 5/04
[52] U.S. Cl. ..................................... 128/83.5; 36/97
[58] Field of Search ....................... 128/83.5, 83, 596; 36/97

[56] References Cited
U.S. PATENT DOCUMENTS

| | | | |
|---|---|---|---|
| 2,497,175 | 2/1950 | Mantos | 36/97 |
| 2,700,832 | 2/1955 | Slovinski | 128/596 X |
| 3,389,481 | 6/1968 | England | 36/97 |
| 3,877,423 | 4/1974 | Tollefsbol | 128/83.5 |

FOREIGN PATENT DOCUMENTS

| | | | |
|---|---|---|---|
| 489338 | 2/1927 | Fed. Rep. of Germany | 36/97 |
| 5360 | of 1826 | United Kingdom | 36/97 |

*Primary Examiner*—John D. Yasko
*Attorney, Agent, or Firm*—Bernard Stickney

[57] ABSTRACT

An adjustable post-surgical shoe having two sole portions which are slidably connected by a pin and tube means and which has a separate means for securing the sole portions in adjusted positions.

7 Claims, 7 Drawing Figures

ADJUSTABLE POST-SURGICAL SHOE

BACKGROUND OF THE INVENTION

The invention relates to a shoe to be worn by a patient after foot surgery. When the patient's foot has sufficiently healed for mobility, there has always been the problem of comfortable foot wear since the usual boxed toe shoe could not be worn. While open slippers or sandals have been used they are not satisfactory in terms of size and security for general wear outdoors or indoors. Surgeons who specialize in foot surgery generally stock various sizes of shoes to be used by their patients when they achieve mobility.

Accordingly it is the primary object of this invention to provide an improved post-surgical shoe which may be adjusted to various sizes.

Another object of this invention is to provide a sturdy adjustable post-surgical shoe having a stable sole construction.

A further object of this invention is to provide an adjustable post-surgical shoe of economical construction.

BRIEF DESCRIPTION OF THE DRAWINGS

These and other objects and advantages of the invention will subsequently become apparent from the following detailed description when read in conjunction with the accompanying drawings wherein.

DETAILED DESCRIPTION OF THE INVENTION AND DRAWINGS

Figure 1:
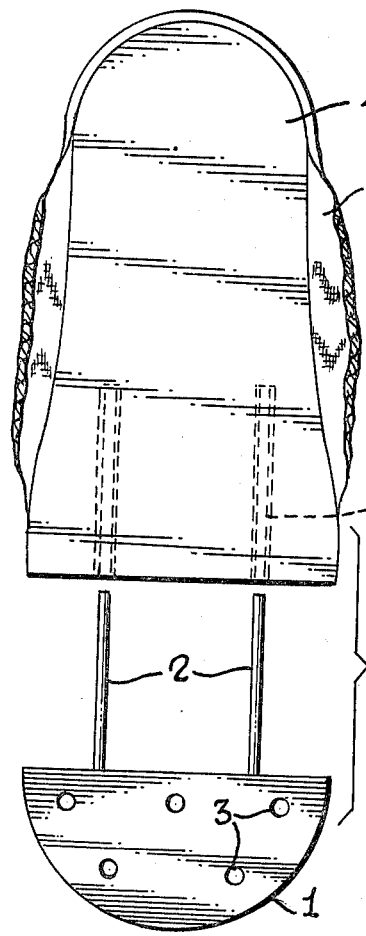
FIG. 1 is a top view of unassembled sole elements of a first modification of the invention.
Figure 2:
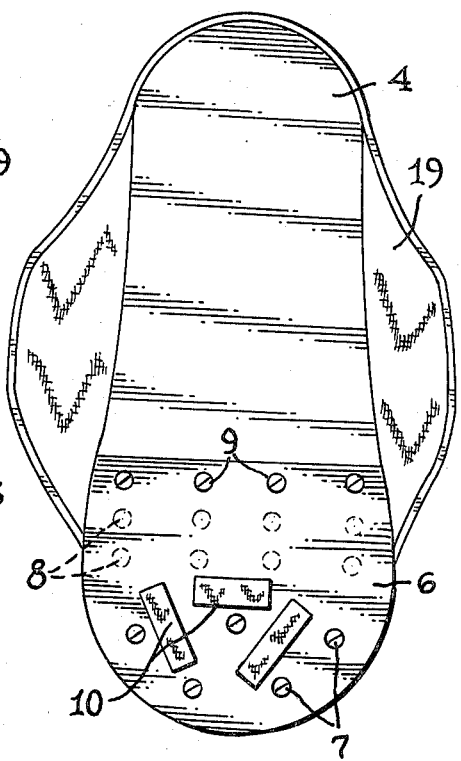
FIG. 2 is a top view of the complete first modification.
Figure 3:
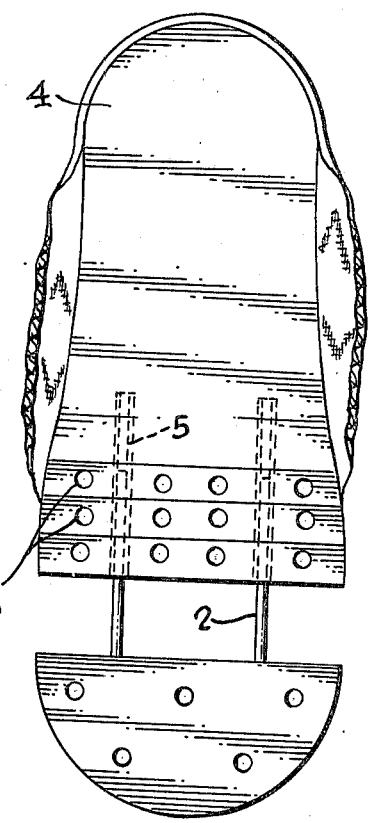
FIG. 3 is a top view of assembled sole elements of the first modification.
Figure 4:
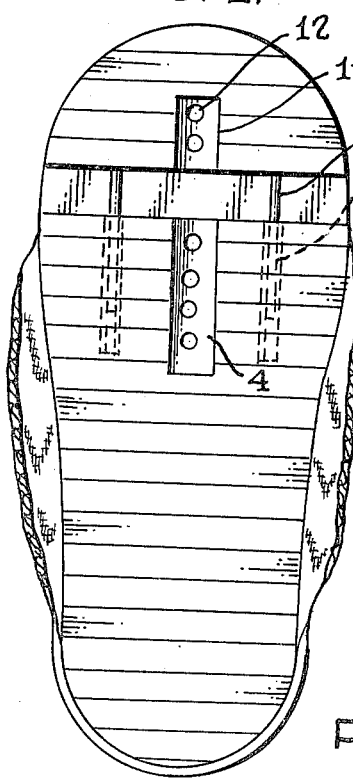
FIG. 4 is a bottom view of the assembled sole elements of a second modification of the invention.

Referring now more specifically to the drawings, FIG. 1 shows a toe element 1 of the sole which may be made of wood and having pins 2 secured therein. Holes 3 are for receiving wood screws 7. Sole element 4 also made of wood has tube inserts 5 aligned to receive the pins 2 as shown in FIG. 3. Shown in FIG. 2 is a metal plate 6 secured to the toe element by screws 7 and also secured to sole element 4 in one of three sets of holes 8 by screws 9. The adjusted position shown is the smallest size obtainable. For larger sizes as shown in FIG. 3, the plate 6 would bridge the gap between the sole elements 1 and 4. Adhesive pads 10 are for securing inner soles to the completely adjusted shoe.

Figure 5:
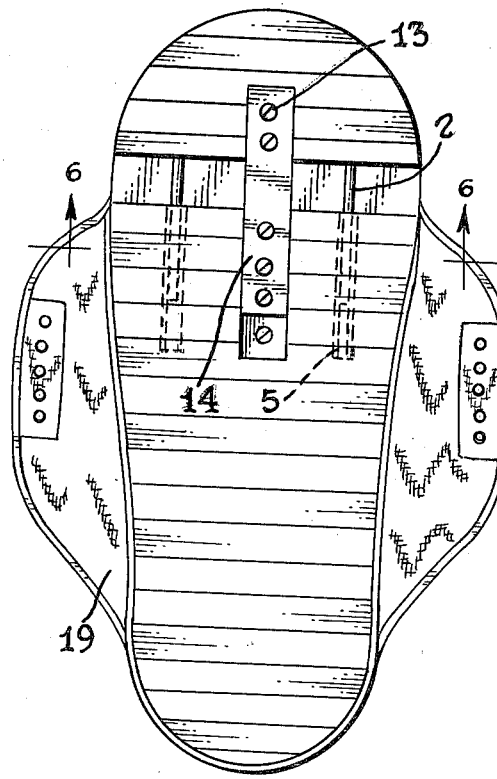
FIG. 5 is a bottom view of the complete second modification.
Figure 6:
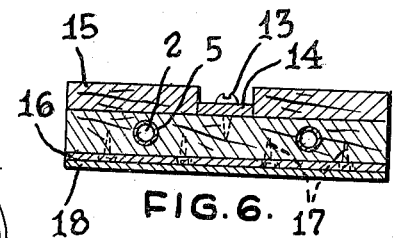
FIG. 6 is a cross-sectional view taken along line 6—6 of FIG. 5.
Figure 7:
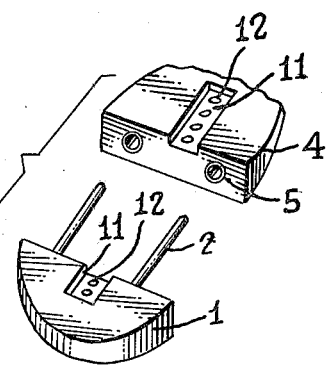
FIG. 7 is a bottom view of unassembled sole elements of the modification.

A second modification for adjusting the post-surgical shoe as shown in FIGS. 4–7 has the same wood block sole elements 1 and 4 with pins 2 and tubes 5. In the bottom of the sole elements, channels 11 are formed with holes 12 for receiving screws 13. As shown in FIG. 5, a metal strap 14 is used to secure the sole elements in various adjusted positions provided by the series of holes 12 in sole element 4. To complete the shoe, an outer sole 15 is attached to the wood sole elements as seen in FIG. 6 and a metal support plate 16 is secured to the wood blocks by screws 17. An inner sole 18 may then be attached to the support plate. Sides 19 which may be made of flexible plastic or canvas complete the post-surgical shoe.

While the sole elements are disclosed as being made of wood which offers a sturdy support base for the shoe and is easily machined for the various connecting means, flexible plastic materials could also be used. In such case, the pin and tube connection serves to provide stability from flexing which would tend to loosen the adjusting connection of FIG. 5 if it were used alone.

While the preferred modifications have been shown and described herein, other changes in the details of construction may be made, but it is to be understood that such changes will be made within the spirit and scope of the present invention.

I claim:

1. An adjustable post-surgical shoe comprising:
   two sole elements,
   first pin and tube connection means slidably connecting said elements for relative movement to one of several positions and second separate means securing the elements in adjusted position.

2. A post-surgical shoe as defined in claim 1 wherein said second means is a plate secured to both sole elements.

3. A post-surgical shoe as defined in claim 1 wherein the sole elements are blocks of wood and the first means are two tubes secured in one of the wood blocks and two pins in the other block and slidably engaged in the tubes.

4. A post-surgical shoe as defined in claim 3 wherein the second means is a metal plate secured to and substantially covering a toe sole element and of sufficient length to be secured to a plurality of positions along the length of the other sole element.

5. A post-surgical shoe as defined in claim 1 wherein the second means comprises channels formed in the sole elements and a strap in the channels secured to both elements.

6. A post-surgical shoe as defined in claim 5 wherein the sole elements are made of wood.

7. A post-surgical shoe as defined in claim 6 wherein the channels are located on the bottom of the sole elements and metal foot support plates as secured to the upper surface of the sole elements.

* * * * *